United States Patent

Van De Vyver et al.

[11] Patent Number: 5,902,556
[45] Date of Patent: May 11, 1999

[54] CATALYTIC GAS SENSOR

[75] Inventors: James Edward Van De Vyver, Lynnwood Manor; Marysia Brodalka, Arcadia; Michael George Howden, Lyttelton Manor; Ian Robert Leith, Lynnwood; Rosalyn Claire Pennefather, Lonehill; Jeremy Rex Wallis, Moreleta Park, all of South Africa

[73] Assignee: Microchip (Proprietary) Limited, South Africa

[21] Appl. No.: 08/624,450

[22] PCT Filed: Oct. 10, 1994

[86] PCT No.: PCT/GB94/02231

§ 371 Date: Jun. 5, 1996

§ 102(e) Date: Jun. 5, 1996

[87] PCT Pub. No.: WO95/10770

PCT Pub. Date: Apr. 20, 1995

[30] Foreign Application Priority Data

Oct. 8, 1993 [ZA] South Africa ............... 93/7479

[51] Int. Cl.[6] .................. F01N 3/10; G01N 25/16
[52] U.S. Cl. .................. 422/174; 422/82.12; 422/83; 422/94; 422/95; 422/96; 422/97; 422/98
[58] Field of Search .................. 422/82.12, 83, 422/94, 95, 96, 97, 98, 174

[56] References Cited

U.S. PATENT DOCUMENTS

| | | | |
|---|---|---|---|
| 4,574,264 | 3/1986 | Takahashi et al. | 338/34 |
| 4,935,289 | 6/1990 | Kikuchi et al. | 428/209 |
| 5,783,154 | 7/1998 | Althianz et al. | 422/98 |

FOREIGN PATENT DOCUMENTS

| | | | |
|---|---|---|---|
| 0377792 | 7/1990 | European Pat. Off. | G01N 27/16 |
| 0446483 | 9/1991 | European Pat. Off. | G01N 27/16 |
| 2216043 | 8/1990 | Japan | G01N 27/12 |
| 2158586 | 11/1985 | United Kingdom | G01N 25/30 |
| 2238617 | 6/1991 | United Kingdom | G01N 25/30 |
| 9102242 | 2/1991 | WIPO | G01N 27/16 |

*Primary Examiner*—Ponnathapura Achutamurthy
*Attorney, Agent, or Firm*—Ladas & Parry

[57] ABSTRACT

A catalytic detector for a flammable gas comprises a substrate and a sensing structure suspended from the substrate. The sensing structure has a combined heating element and temperature sensing element in the form of a layer-deposited electrically conductive track terminating in at least two electrically conductive bridging leads. A catalytic bead is deposited over the temperature sensing element and that portion of the substrate which is directly beneath the sensing structure is etched away so as to isolate thermally the sensing structure with the temperature sensing structure being supported by the bridging leads. The electrically conductive track is sandwiched between a substrate adhesion layer for facilitating adhesion of the conductive track and a superstrate diffusion barrier layer. The invention extends to a method of manufacturing a gas detector and a sensing structure.

16 Claims, 5 Drawing Sheets

CATALYTIC GAS SENSOR

BACKGROUND OF THE INVENTION

This invention relates to a catalytic gas detector, and to a method of manufacturing such a detector.

Catalytic gas detectors are used in the continuous monitoring of atmospheres to detect the presence of a low molecular weight flammable gases, such as methane. The principle of operation relies on the fact that small concentrations of hydrocarbon gases are cationically oxidized in air at elevated temperatures over a suitable catalyst such as palladium rhodium, platinum or iridium. The resultant exotherm reaction produces a temperature rise which is sensed by a sensor. There is a direct relationship between the degree of temperature rise and the proportion of combustible gas in the atmosphere being measured.

Sensors of the type described, which are commonly known as pellistors, comprise a coil of a noble metal, such as platinum, covered with a bead of porous catalytic material. The change in temperature referred to above leads to a change in resistance of the coil, which is detected in a Wheatstone bridge-type configuration of which the coil forms a part.

In the case of portable sensing instruments which are reliant on battery power, it is important that the power consumption of the pellistor be as low as possible.

There are two ways of achieving this end:

(i) By increasing the electrical resistance of the wire;

(ii) By decreasing the amount of heat that is lost from the pelestor to its surroundings;

In order to satisfy the first requirement, published UK patent application GB2238617A describes a thin wire in the form of a conductive track deposited on a non-conductive and thermally isolating layer, such as silicon nitride or silicon oxde, which is deposited upon the silicon substrate. Photolithographic processes are commonly used to define the conductive track or heater element. The bead is usually formed by the deposition of a material such as porous alumina on top of the heater element.

In order to satisfy the second requirement, the substrate beneath the isolating layer is generally etched away so that a suspended membrane is formed upon which the heater element is located, thereby increasing the thermal isolation of the heater element, which results in a significant decrease in power consumption. This is important for portable sensing instruments which are reliant on battery power.

SUMMARY OF THE INVENTION

According to a first aspect of the invention there is provided a catalytic detector for a flammable gas comprising a substrate and a sensing structure suspended from the substrate, the sensing structure including:

a) a heating element;

b) a temperature sensing element in the form of a layer-deposited electrically conductive track terminating in at least two electrically conductive bridging leads;

c) a catalytic bead associated with the temperature sensing element, that portion of the substrate which is directly beneath the sensing structure being etched away so as to isolate thermally the sensing structure, and the temperature sensing structure being supported by the bridging leads.

Preferably the leads extend from the conductive track to terminal pads supported on the substrate, the leads having a thickness and cross-sectional profile which allows them to provide complete support for the sensing structure.

Conveniently, the electrically conductive track is sandwiched between a substrate adhesion layer for facilitating adhesion of the conductive track and a superstrate diffusion barrier layer.

Typically the adhesion layer and the diffusion barrier layer are arranged to prevent buckling or twisting of the conductive track when subjected to thermal stress.

The catalytic bead advantageously comprises a catalyst precursor distributed within a refractory carrier.

The refractory carrier typically comprises alumina and the catalyst precursor comprises palladium (II) chloride or palladium (II) nitrate.

Preferably the heating and temperature sensing elements are combined in the form of a single integrated layer-deposited meandering track of platinum.

Typically, the substrate is formed from a planar wafer of single crystal silicon having a base face and a top face, the base face of the wafer being coated with an inert film and the top face being coated with a dielectric film, with the inert film being a silicon dioxide film and the dielectric film being an alumina film.

The leads may have a thickness matching that of the track and a U-or V-shaped cross sectional profile.

The invention extends to a method of manufacturing a catalytic gas detector comprising the steps of:

a) providing a substrate;

b) depositing a heating and temperature sensing element in the form of at least one conductive track onto the substrate;

c) etching away that portion of the substrate directly beneath the conductive track so as to define a cavity over which the conductive track is suspended, with bridging conductors extending between the conductive track and terminals on the substrate; and d) depositing a catalyst with a refractory carrier onto the conductive track so as to form a sensing structure supported by the bridging conductors.

In a preferred form of the invention, the method includes the step of depositing a dielectric thin film onto the substrate, the film being chosen from a material which serves as a diffusion barrier, as an adhesion layer for facilitating adhesion of the conductive track and having a thermal expansion coefficient which matches that of the conductive track.

The dielectric thin film is typically formed from alumina and the substrate is a silicon wafer.

Conveniently, the method includes the step of annealing the catalytic gas detector in a single step for stabilizing the electrical properties of the platinum, and for facilitating adhesion and cohesion of the catalyst and carrier and conditioning of the catalyst.

According to a still further aspect of the invention there is provided a method of manufacturing a sensing structure for a catalytic gas detector comprising the steps of:

a) depositing a conductive track onto a substrate;

b) preparing a catalyst comprising a noble metal on a refractory carrier by treating the catalyst with a catalyst precursor so as to form a slurry or paste;

c) applying the slurry or paste to the conductive track by screen printing or stenciling; and d) calcining the slurry or paste in air.

Preferably, the method includes fiber steps of preparing a compensating or reference element by treating or "poisoning" the refractory carriers which may be alumina, with an alkali metal, and preparing the catalyst by wet milking a palladium (II) chloride catalyst precursor with sub-micron alumina powder, with the palladium particles, formed on subsequent calcite at around 750° C., fulfilling a double function as catalyst and binding agent.

Typically, the catalytic activity of the sensing elements is enhanced by repeatedly heating the elements at a higher temperature than the operating temperature of between 700° C. and 800° C. in a methane/air mixture, for approximately two minutes at a time.

The binding agent may be a colloidal silica dispersion of 15% to 30% by weight content and average silica particle size in the region of 8 nm, binding being accomplished by heading the sensing element, after the paste or slurry has been deposited onto the conductive element, to a temperature of 900° C. to 1000° C.

In one form of the invention, an organic solvent is combined with ethyl cellulose, the alga and the glass frit to obtain a paste, which is stenciled onto the conductive element and calcined in air at a temperature of 600° C. to 800° C.

The catalyst may be prepared by calcination with an alumina precursor and an acid, in which activated alumina is mixed in a predetermined ratio of approximately 2:1 by weight, with the addition of 1% or less by weight of a pelting agent, with calcination taking place in air at 700° C. to 800° C. for approximately 30 minutes.

Advantageously, the method includes the step of spraying a solution of the catalyst and carrier paste through an aligned shadow mask onto the track from both sides of the base.

DESCRIPTION OF EMBODIMENTS

Figures 1, 2, 3, 4A, 4B, 4C:
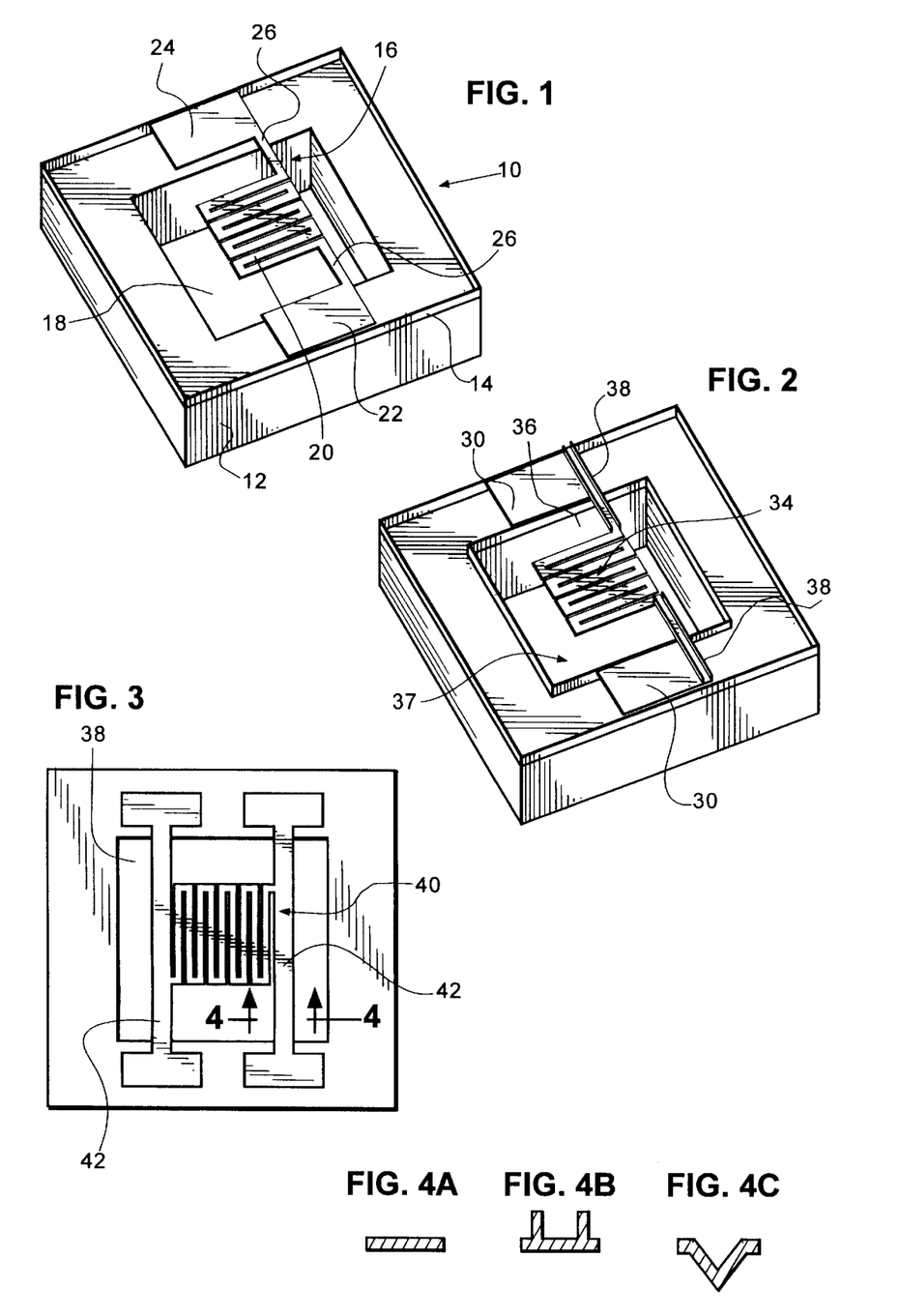
FIG. 1 shows a schematic perspective view of a first embodiment of a detector of the invention.
FIG. 2 shows a perspective view of a second embodiment of a detector of the invention.
FIG. 3 shows a top plan view of a third embodiment of a detector of the invention.
FIG. 4A to 4C show alternative cross sectional views on the line A—A of FIG. 3.

Referring first to FIG. 1, a first rudimentary embodiment of a detector 10 is shown comprising a substrate 12 formed from a (100) oriented silicon wafer using conventional semi-conductor processing techniques. The substrate is between 0.3 and 0.5 milimetres thick, and has a membrane 14 deposited on its uppermost surface. The membrane may be formed from one or more layers of different materials comprising a refractory oxide, a nitride or a combination thereof. Suitable materials are typically $SiO_2$, $Si_3N_4$, SiON, $Al_3N_4$, TiN and $Al_2O_3$.

An atomic diffusion layer may also be provided, for which Ti/W, Ti/W-N or $Al_2O_3$ may be used. The composition of the membrane is a key factor in the successful operation of the sensor, and must have certain properties, including low thermal conductivity, good adhesion, thermal shock resistance, matched thermal expansion to silicon and to platinum low atomic diffusively, mechanical strength free of mechanical stress and low electrical conductivity. Such properties are displayed by some of the materials described above.

A temperature sensing element 16 bridges a cavity 18 etched through the centre of the substrate 12 and the membrane 14. The temperature sensor 16, which doubles as a heater element, comprises a central free-standing meander 20 and a pair of terminal pads 22 and 24 resting on the membrane 14 and supporting the meander 20 via bridging leads 26. In order to provide long term adhesion at elevated temperatures between the membrane 14 and the meander 20, additional metallic or oxide adhesion layers may be required, where these are not provided by the division layer. Typically, such layers will be formed from Ti/W, Cr, NiCr or $Al_2O_3$.

In order to minimize thermal losses and to provide sensors with the lowest possible power consumption and relatively quick response times, silicon is removed from the substrate so as to provide the recess 18. Any method of silicon removal commonly used in semiconductor manufacturing processes may be adopted. Typically, the anisotropic etching characteristics of (1-0-0) silicon in certain wet etching techniques are employed to provide precise wall angles and final dimensions.

In FIG. 2, a free-standing meander 34 is shown in which all of the membrane material is removed from beneath the sensor element 36 so as to define a cavity 37. Free suspension of the meander results in minimum heat losses. Structural strength is achieved by increasing the thicknesses of the leads 38 which extend between the terminal pads 30 and the meander 34. It is clear from FIG. 2 how the structural strength of the electrical bridging leads 38 is increased by forming them with a U-shaped profile. The U-shaped profile provides a reduced thermal conducting area so as to reduce conductive heat loss through the leads. The leads 38 may be thickened either by sputtering, electroplating or electroless-plating methods.

In the simplest embodiments of the sensor illustrated in FIGS. 1 and 2, the functions of the heater and the temperature sensing elements 16 are combined by using a meandering track of pure platinum or an alloy thereof.

The geometry and thickness of the platinum meander are chosen so as to provide an optimum sensitivity for the sensor as a compromise between the heater and temperature sensing elements.

An ideal heater material differs substantially from an ideal temperature sensing material which operates on the principle of linear changes in resistivity due to temperature changes. Heater operation is based on a high resistivity material releasing heat in response to an electrical current passing through the materials with the result that an ideal heater material must have the properties of high electrical resistivity, resistance against electro-migration and a low temperature co-efficient of resistance. In contrast, an ideal temperature sensing material has a temperature co-efficient of resistance which is both high and linear.

In FIG. 3 an alternative embodiment of a free-standing temperature sensor and heater 40 is shown, and is in the form of an H-shaped configuration in which the recess 38 is spanned by parallel leads 42. The leads may have a flat cross-sectional profile of the type illustrated in FIG. 4A. Alternatively, the structural strength of the leads 42 may be increased by forming them with angled or U-shaped cross-sectional profiles of the type respectively illustrated in FIGS. 4B and 4C.

Figure 5A:
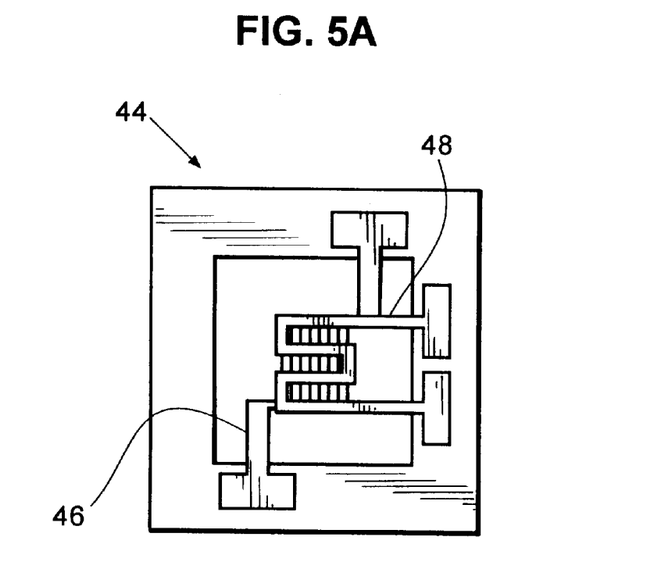
FIG. 5A and 5B show top plan views of a fourth embodiment of a detector of the invention.
Figure 5B:
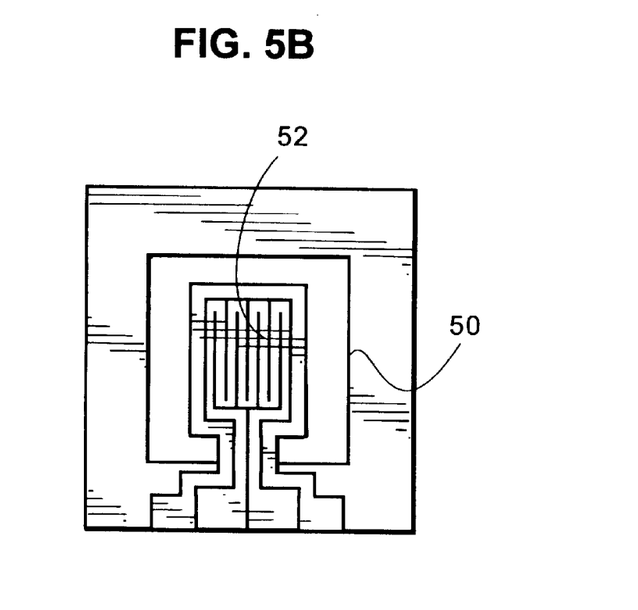

Turning now to FIGS. 5A and 5B, more sophisticated embodiments of sensors are shown in which separate heating and sensing elements are provided. In FIG. 5A, a sensor 44 comprises a sensing element 46 and a heating element 48 positioned above the sensing element 46.

In order to provide electrical isolation between the heating and temperature sensing elements in the vertical configuration illustrated in FIG. 5A, a suitable insulating film such as $Al_2O_3$ is deposited on top of the heater, and is followed by a track of platinum which acts solely as a resistance thermometer. In the horizontal configuration illustrated in FIG 5B, a heater element 50 encircles a temperature sensing element 52, which is in the form of a resistance thermometer, and no electrical isolation between the heater 50 and the thermometer 52 is required.

During a production run, many sensors are manufactured on a single wafer. Typically, a production run includes a batch of between ten and twenty wafers. In the following description of the production process there is reference to only one of the sensors on a single wafer.

Each wafer is formed from (1-0-0) oriented single crystalline silicon, with surfaces that are polished on both sides. The anisotropic etching behavior of the crystalline silicon is essential in the controlled removal of the silicon from beneath the active area constituted by the heating element. In order to restrict the etching of the silicon to a specific area, the layers 56 and 58 are formed from an inert masking material such as $SiO_2$, $Si_3N_4$ or various precious or refractory metals. The masking material is then coated by a photosensitive resist which is subsequently exposed with ultra-violet light through a patterned chrome mask, thereby transferring the pattern onto the resist which is developed, and removing the unexposed resist from the masking material. By etching the masking material away where there is no resist, the pattern is transferred so as to define the channels 60 illustrated in FIGS. 6B and 6C. After this step, the resist is removed.

The described photoresist technique is applied, with minor modifications, to the transfer of the relevant pattern to each of the process steps. I the present case, the material from which the membrane is formed can be used as a mask for the anisotropic etching of silicon. A layer for the membrane 56 is deposited onto the top surface of the silicon wafer 54 by means of a plasma enhanced chemical vapor deposition (PECVD) process to a thickness of about 1 $\mu$m. The lower membrane 58 is coated with a $SiO_2$ layer deposited by means of a chemical vapor deposition (CVD) process.

Platinum from which the heating element is formed, is a chemically unreactive material. This means that a photoresist pattern would be extremely difficult to transfer to an underlying platinum layer by means of a chemical etching.

Figure 6A:
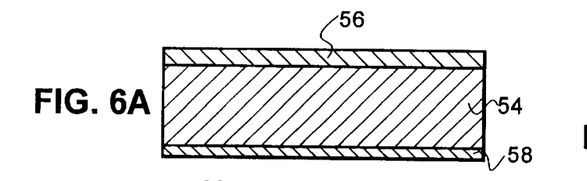
FIG. 6A to 6K show cross-section and perspective views of various stages in a first embodiment of a method of manufacturing a detector of the invention.
Figure 6B:
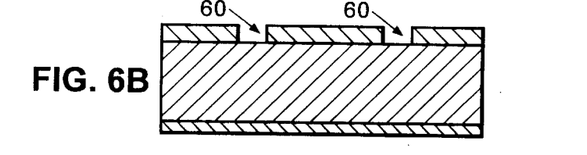
Figure 6C:
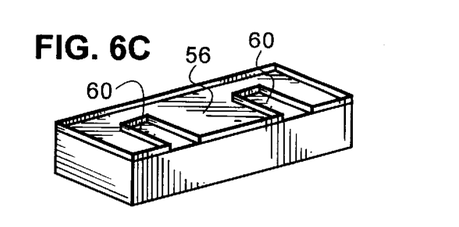
Figure 6D:
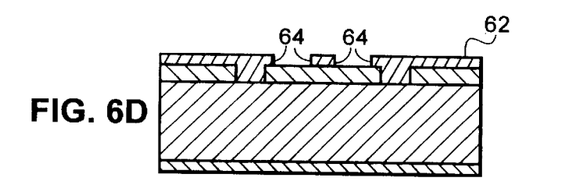

In order to overcome this problem, a lift-off process is utilised, in which a resist 62 is formed on the $SiO_2$ membrane 56 in the manner illustrated in FIG. 6D. Alternatively, another etching process such as ion beam milling may be used. The resist 62 is patterned with overhanging side walls 64. As is clear from FIG. 6E, an adhesion and barrier layer against metal or silicon diffusion 66 is deposited on the resist 62, followed by a layer of platinum 68. The overhanging side walls have the effect of breaking the continuity of the platinum layer across the pattern boundaries, thereby delineating the meander 70 and exposing the overhanging side walls of the resist to chemical removal by a solvent or an acid solution. When the resist 62 is removed by such a solution, then only the platinum meander 70 remains, as is clear from FIGS. 6F and 6G.

Figures 6E, 6G:
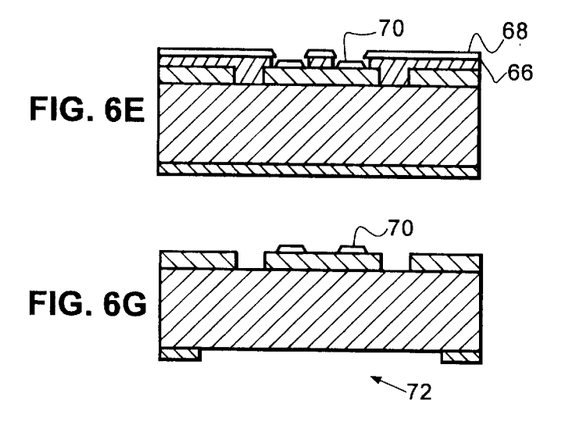
Figure 6F:
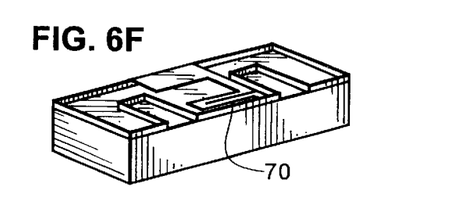
Figure 6H:
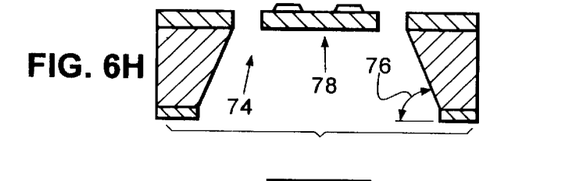

After the first pattern constituted by the slots 60 has been applied, the following patterns have to be accurately aligned with the patterns of the previous step. An optical microscope and an x-y table with rotation around the z-axis is used to align the wafer to the patterned chrome mask. The lower $SiO_2$ layer 58 is etched away so as to provide a recess 72. As silicon is opaque to the visible spectrum, the etching pattern for the lower membrane 58 is aligned with the uppermost pattern by using a light source for which silicon is transparent. An infrared camera is used for this purpose, in order to align optically the chrome mask pattern with the pattern on the upper membrane 56 prior to etching. After the $SiO_2$ has been etched away, the structure illustrated in FIG. 6G is ready for the silicon etch. The silicon wafer 54 is then etched away anisotropically by means of an Ethylenediamine Pyrocatechol (EDP) solution, which has a fast silicon etch rate and only attacks weakly the masking materials employed. Other possible wet etching solutions are potassium hydroxide, hydrazine and ammonium hydroxide.

Figure 6I:
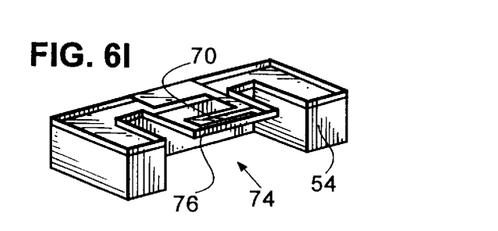
Figure 6J:
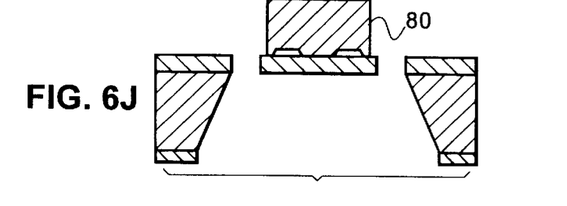
Figure 6K:
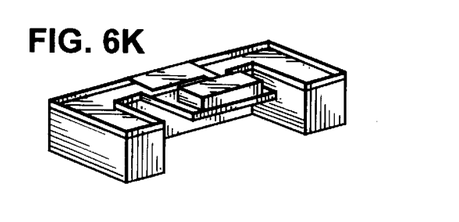

Owing to the crystal orientation of the silicon wafer, the side walls of the silicon are characteristically inched at an angle of 54.7 degrees from the horizontal, as is illustrated at 76 in FIG. 6M. As is clear from FIG. 6I, the sensor has a meandering heater element 70 carried on the patterned membrane 56 and suspended over the cavity 74 in the silicon support structure. The silicon wafer 54 is mounted onto a plastic sheet, and each sensor is diced or sawed along its border by means of a diamond saw in order to separate it from its neighbors without affecting its relative position. V-shaped grooves can also be etched into the wafer, thereby enabling the wafer to be easily separated into chips, without the need for dicing. As a final step, a catalyst comprising a noble metal deposited on a refractory carrier 80 is applied to the active area defined by the suspended heater element 78.

Typically, the catalyst and refractory car is mixed into a paste, which is applied simultaneously onto the entire wafer by means of screen printing. This results in the positioning of a well defined dot of catalyst on every sensor. The paste is dried and sintered prior to dividing up of the wafer. Alternatively, individual sensors may be packaged, electric connected and heated electrically in a methane atmosphere.

Figure 7A:
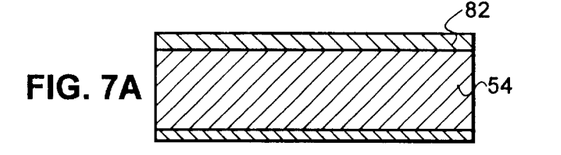
FIG. 7A to 7L show cross-sectional and perspective views of various stages in a second embodiment of a method of manufacturing a detector of the invention.
Figure 7B:
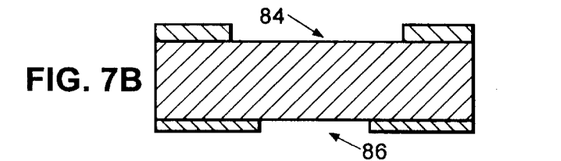
Figure 7C:
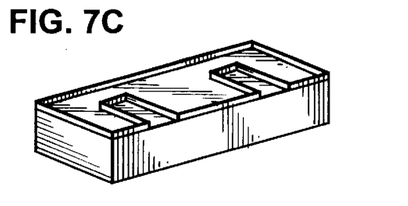
Figure 7D:
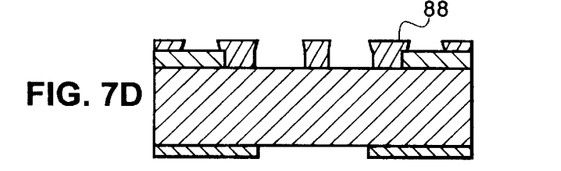
Figure 7E:
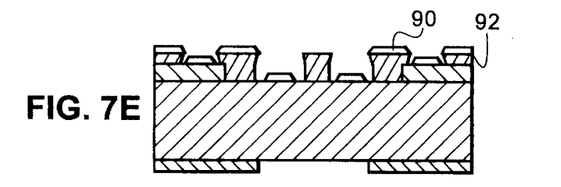
Figure 7F:
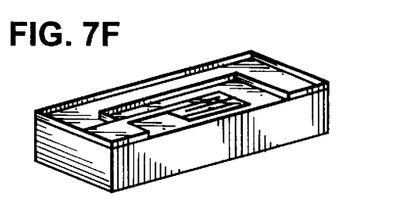

The top and bottom surfaces of the wafer are patterned in the same manner as was described with reference to FIG. 6B so as to provide upper and lower recesses 84 and 86 illustrated in FIG. 7B. A resist pattern 88 is then applied, followed by a layer of platinum 90 preceded by the required adhesion and barrier layer against metal/Si diffusion 92. The layers 90 and 92 are applied by a combination of sputtering followed by a lift-off process.

The top $SiO_2$ layer 82 may be changed for an adhesion and metal diffusion barrier layer 92, thereby reducing the complexity and matching the thermal expansion coefficients of the different layers. For this $Al_2O_3$ is typically used.

Figure 7G:
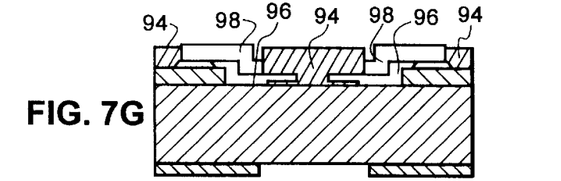
Figure 7H:
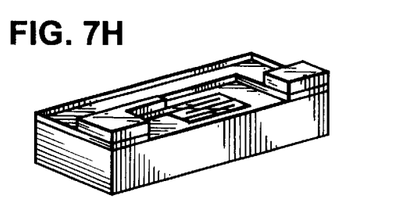
Figure 7I:
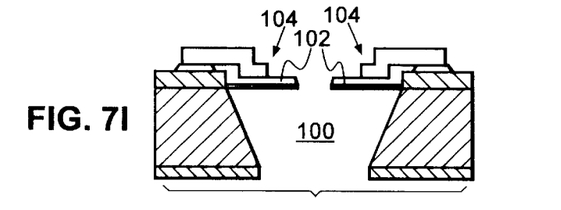
Figure 7J:
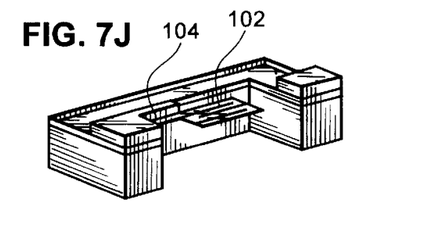

Referring now to FIG. 7G, a fiber resist pattern 94 is applied followed by application of platinum layers 96 and 98 so as to define thickened leads. The layer 98 is applied by way of sputtering or plating and after the resist 94 is stripped away, the silicon wafer is etched anisotropically so as to define a cavity 100 illustrated in FIG. 7I. The resultant structure of FIG. 7J comprises a heating element in the form of a platinum meander 102 suspended from the support structure by the platinum bridging leads 104.

Figure 7K:
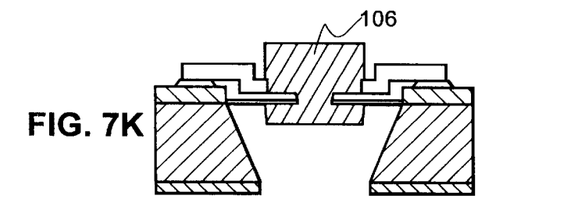
Figure 7L:
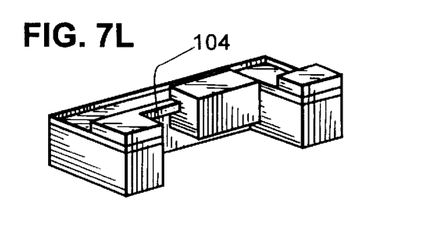

A catalyst and refractory carrier 106 is then applied by spraying a solution of the paste through an aligned shadow mask onto the active area constituted by the heater element 102. An additional improvement is to apply the same catalyst and refractory carrier using the same method from the base of a silicon wafer 54 so as to fully coat the heater element. The mask for this step is formed by the lower surface of the wafer structure instated in FIG. 7K.

The embodiment illustrated in FIGS. 5A and 5B utilizing separate heater and temperature sensors may be manufactured using either of the methods illustrated in FIGS. 6A to 6K or 7A to 7L. Packaging of the sensors is performed using a standard procedure of the type applied to discrete electronic components such as transistors. The individual die is removed from the plastic sheet upon which the wafer was attached during dicing, and is mounted onto a standard transistor header using an epoxy cement. After the epoxy has hardened thin aluminum wire is used to connect electrically the heater element with the wire posts on the heater. A lid having a upper aperture is then welded onto the header so as to protect the sensor.

Figure 8A:
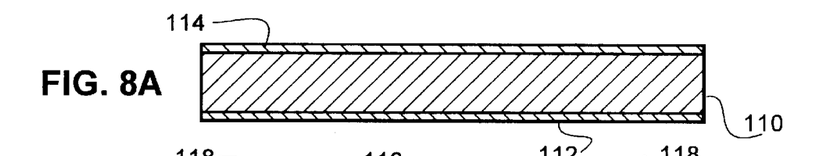
FIG. 8A to 8E show cross-sectional views of various stages in a third embodiment of a method of manufacturing a detector.

Referring now to FIGS. 8A to 8E, cross-Seton views of various stages in the manufacture of a preferred embodiment are shown. In FIG. 8A, a polished silicon wafer 110 having a (1-0-0) crystal orientation is formed having a Silicon dioxide layer 112 as a base on an operatively lower face of the silicon wafer 110 and a dielectric thin film of alumina 114 having a thickness of 0.2 to 03 $\mu$m is deposited on the operatively upper face of the silicon wafer 110 using conventional thin film processes.

Figure 8B:
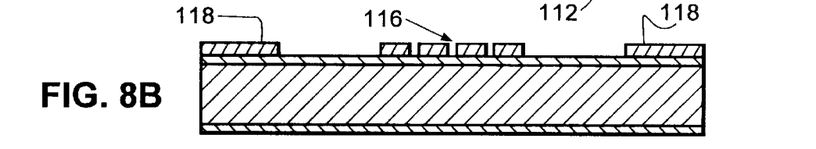
Figures 8C, 8D:
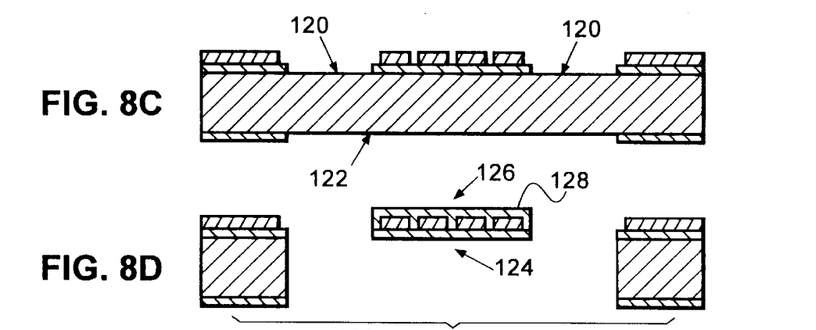
Figure 8E:
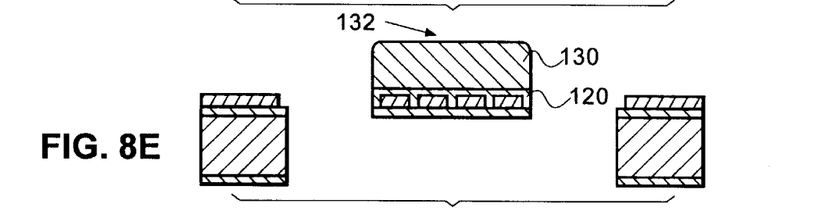
Figure 9:
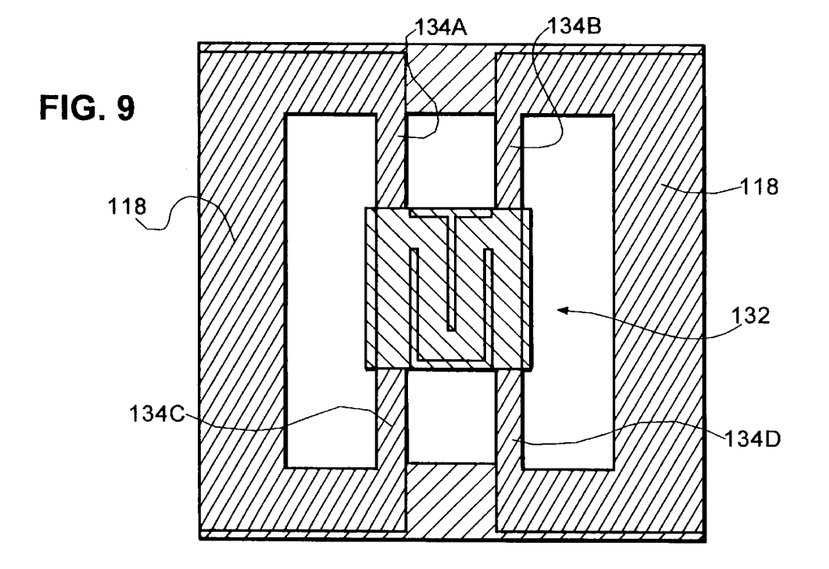
FIG. 9 shows a top plan view of the completed detector of FIG. 8E.

As is clear from FIG. 8B and FIG. 9, a platinum layer having a thickness of 1.8 $\mu$m to 2.2 $\mu$m and comprising a central meander structure 116 flanked by outer electrically conductive terminal layers 118 is deposited on top of the alumina layer 114. The alumina layer is selected to match the thermal expansion of the platinum, thereby minimizing stress build-up between adjoining layers. The platinum layer is deposited and patterned using standard techniques developed for the micro-electronics industry. The dielectric alumina layer and the inert layer of silicon dioxide are patterned using similar techniques. The alignment of the top and bottom patterns is accomplished by infra-red light to render the silicon transparent. Other alignment techniques may also be used. After the dielectric and inert layers 112 and 114 have been etched away and patterned, as is illustrated at 120 and 122 in FIG. 8C, a cavity 124 is etched away using silicon etchants having anisotropic behavior, thereby creating a suspended meander structure 126.

A dielectric layer 128 of alumina of 1 $\mu$m thickness is deposited on the meander structure so as to strengthen it and to act as a barrier layer against diffusion from a catalytic layer or bead 130 which is subsequently deposited on top of the dielectric layer 138. The catalyst is contained within a thick film paste which is deposited onto the meander structure by means of screen-printing or other thick film techniques, resulting in a final suspended sensing structure 132. In FIG. 9, the double-O configuration defined by the platinum layer can clearly be observed, as can the meander structure, with the meander structure 132 being supported entirely on four platinum bridging leads 134A, 134B, 134C and 134D also having a thickness of 1.8 $\mu$m to 2.2 $\mu$m.

The gas sensitive layer is composed of a calcined activated alumina onto which a noble metal catalyst is deposited. Palladium (II) chloride or palladium (II) nitrate are commonly used as catalyst precursors. The nitrate salt does have the advantage that no chlorides, which could have an inhibiting effect, remain on the alumina.

In a preferred version of the catalyst manufacturing process, the palladium (II) chloride precursor is milled with sub-micron sized (down to diameters of a few nm) alumina to reduce the size of the palladium chloride particles, using methanol as a solvent. The ratio of palladium chloride to alumina is about 25% by weight. The high palladium content results in the metal actually binding the alumina particles together. After milling, most of the methanol is removed by evaporation, and the addition of a terpineol/ethyl cellulose organic vehicle yields a screen-printing paste suitable for screening or stenciling. In the other methods of catalyst preparation (using silica sol, glass frit and alumina precursor or acetic acid as binders) the base material is prepared by a standard impregnation process for the deposition of the palladium precursor material on the support. The alumina powder is typically soaked for several hours in a solution of palladium (II) chloride in aqueous hydrochloric acid. The hydrochloric acid and water is then slowly evaporated.

The base material of which the compensating or reference element is composed can be the same alumina with most of its activity removed by poisoning the active sites with potassium. This is achieved by soaking alumina in a potassium hydroxide/water solution containing 5% to 10% by weight of potassium hydroxide for several hours. The water is slowly evaporated and replaced by methanol as the vehicle for screen printing. A solution of ethyl cellulose in terpineol is also added to improve the screen printing properties of the paste. The reference elements are calcined under the same conditions as the active elements, i.e. calcination in air at 750° C. for approximately 30 minutes. This treatment has been found to remove most of the activity to hydrogen which is essential for correct operation in an atmosphere containing hydrogen gas in amounts below the lower explosive limit.

In an alternative method of poisoning, an alumina element, either with or without potassium hydroxide, is covered with a thin layer of sodium silicate glass. The sodium silicate (or water glass) is a 50 wt % $SiO_2$ solution in water. This is diluted to a 25 wt % $SiO_2$ solution which is then applied to the degassed reference elements. The sodium silicate may also be incorporated into the bulk of the reference elements. After a drying time, the reference elements can be cured either electrically or thermally by heating in a furnace.

In the case of the preferred version of the active elements (palladium chloride milled with alumina) an inorganic binding agent is not needed. This function is filed by palladium particles finely dispersed throughout the bulk of the element.

In order to improve the adhesion of the alumina paste to the meander, it is feasible to screen a glass frit paste (a lead-free glass frit of particle size <10 microns mixed with terpineol or ethyl cellulose) onto the platinum meanders, subsequently drying, and then screening the alumina paste onto the glass frit and calcining in the usual way, at 750° C. for 30 minutes.

After calcination, the catalytic activity of the sensors is increased and stabilized by repeatedly heating at a higher temperature than the operating temperature in a methane/air mixture for two minutes at a time, until the activity has stabilised, as is indicated by sensitivity measurements. This process is known as conditioning.

After conditioning, the preferred version sensors yielded a sensitivity of up to 100 mV when operated in 2,5% methane in air at a voltage of 2V in a Wheatstone bridge test circuit.

There are three alternative methods in which an inorganic binding agent and the active and reference materials may be applied to the platinum meander. One process uses a binder, colloidal silica or silica sol, which is effective at high calcination temperatures (900–1000° C.) the other two processes use glass frit and an alina precursor, both of which are effective at lower calcination temperatures (600–800° C.).

In the first process, the binding agent is an aqueous colloidal dispersion of 15 to 30 wt % content and 8nm silica particle size. This is added to the dry base material of both the active and reference elements and mixed to form a stiff paste, which is suitable for printing through a stencil or a screen with square openings of 0.35–0.45 mm per side. The stencil yields alumina layers of 100 micron thickness, while it is possible to obtain layers of 20–30 micron thickness after sintering when using a screen, resulting in a reduced load on the free-standing sensors.

After these processes, binding is accomplished by slowly heating the detectors in air to a maximum temperature of 900–1000° C. and slowly cooling them down again. Low temperature binding processes have definite advantages, such as the reduced loss of surface area and reduced thermal stresses.

In the second process, which can be used for low temperature binding and which contains an inorganic binder, 5–20 wt % glass frit is used. 12% wt glass frit is preferably used in the process of the invention to obtain maximum strength and minimum interference with catalytic activity. The glass frit is milled with alumina for one hour to obtain a mixture in which the frit is of fine particle size and is well distributed.

The powder is then calcined above 400° C. (which is above the glass transition temperature) for an hour to allow a certain amount of reaction between the glass frit and the alumina to take place.

Terpineol, an organic solvent with a high boiling point, combined with ethyl cellulose, is used as a medium to obtain a paste of the correct viscosity for screen printing.

The same steps as in the first process are used to apply the alumina mixture to the free-standing platinum meander, with the exception that terpineol and not water is used to adjust the viscosity as necessary. After application the sensors are dried and calcined at a temperate of 600–800° C. in air.

In the last process for the low temperature binding of alumina, the alumina is calcined with an alumina precursor and an acid. Activated alumina is mixed in a ratio of two parts by weight to one with an alumina precursor, such as aluminum nitrate, with the addition of 1 wt % or less of acetic acid. The acid acts as a pelting agent. Enough water is added to give either a screen printing paste of the correct viscosity, or a slurry for applying small drops to the free-standing meanders. Calcination is performed in air for 3 hours at 750° C. The surface area after calcination is in excess of $200m^2g^{-1}$ if a high surface area activated alumina is used as the starting material. Gradual warm up (100° C. per hour or less) and slow cool down is a feature of the heat treatment or calcination step in all binding processes.

The sensors (all three catalyst and carrier combinations) were found to be linear in their reaction to methane concentrations of up to 2.5% in air. It was also found that the sensors are equally suitable for the detection of hydrogen and methane gas at operating temperatures.

For instance, a combination of 0.35% $H_2$ and 1.05% $CH_4$ yields the same signal as 1.4% methane in air. The operation of the sensors is also uneffected by the reduction of oxygen concentration from 21% to 13%.

By using the bridging leads as a support for the sensing structure, the simplicity of manufacturing is enhanced. Further, the overall structural strength and flexibility of leads formed from platinum or a similar noble natal results in a more resilient structure than one in which major support for the sensing structure is provided by a relatively brittle $SiO_2$ membrane or the like.

We claim:

1. A catalytic detector for a flammable gas comprising a substrate and a sensing structure suspended from the substrate, the sensing structure including:
   a) a heating element;
   b) a temperature sensing element in the form of a compact layer-deposited electrically conductive meander terminating in at least two electrically conductive bridging leads extending from the meander to terminal pads supported on the substrate; and
   c) a catalytic bead supported by and covering the meander, the catalytic bead and the meander in conjunction defining a monolithic structure;
   that portion of the substrate which is directly beneath and alongside the sensing structure and the bridging leads being etched away so as to define a cavity which isolates thermally the sensing structure, the bridging leads having a thickness and cross-sectional profile which allows them to provide substantially complete support for the sensing structure.

2. A catalytic detector according to claim 1 in which the meander is sandwiched and encapsulated between a substrate diffusion barrier layer and a superstrate diffusion barrier layer, the diffusion barrier layers being selected so that they have substantially the same thermal expansion co-efficients as that of the heater element, thereby preventing buckling or twisting of the conductive meander when subjected to thermally induced stress.

3. A catalytic detector according to claim 1 in which the bridging leads extend alongside one another and span across the enter width of the cavity, with the electrically conductive meander and the catalytic bead spanning and being supported by the bridging leads, and each of the bridging leads being connected to separate term pads.

4. A catalytic detector according to claim 3 in which the sensing structure has an H-configuration, with the bridging leads forming the legs of the H and the meander and the catalytic bead forming the cross arm of the H.

5. A catalytic detector according to claim 1 in which the bridging leads have a U- or V-shaped cross-sectional profile.

6. A method of manufacturing a sensing structure for a catalytic gas detector comprising the steps of:
   a) depositing a heating and temperature sensing element onto a substrate, the heating and temperature sensing element comprising a compact conductive meander terminating in at least two conductive bridging leads;
   b) etching away that portion of the substrate directly beneath and alongside the conductive meander so as to define a cavity over which the conductive meander is suspended, with the bridging leads extending between the conductive meander and terminals on the substrate;
   c) preparing a catalyst comprising a noble metal on a refractory carrier by treating the catalyst with a catalyst precursor so as to form a slurry or paste;
   d) applying the slurry or paste to the conductive meander so as to form a sensing structure supported by the bridging leads; and
   e) calcining the slurry or paste in air.

7. A method according to claim 6 in which the slurry or paste is applied to the conductive meander by screen printing, stenciling, spraying or other thick film techniques.

8. A method according to claim 6 which includes the farmer step of preparing a compensating or reference element by treating or "poisoning" the refractory carrier with an alkali metal.

9. A method according to claim 8 which includes the further step of preparing the catalyst by wet milling a palladium (II) chloride catalyst precursor with sub-micron alumina powder, with the palladium particles formed on the subsequent calcination step fulfilling a double function as catalyst and binding agent.

10. A method according to claim 6 which includes the step, prior to calcining the slurry or paste in air, of drying the slurry or paste in air to remove volatile components of the paste.

11. A method according to claim 6 in which the catalytic activity of the sensing element is enhanced by repeatedly heating the element at a higher temperature than the operating temperature in a methane/air mixture.

12. A method according to claim 10 including a binding agent which is a colloidal silica dispersion of 15% to 30% by weight content and average silica particle size in the region of 8 nm, binding being accomplished by heating the sensing element, after the paste or slurry has been deposited onto the conductive meander, to a temperature of 900° C. to 800° C.

13. A method according to claim 6 in which an organic solvent is combined with ethyl cellulose, the alumina and the glass frit to obtain a paste, which is stenciled onto the conductive element and calcined in air at a temperature of 600° C. to 800° C.

14. A method according to claim 6 in which the catalyst is prepared by calcination with an alumina precursor and an acid, and in which activated all is mixed in a predetermined ratio of approximately 2:1 by weight, with the addition of 1% or less by weight of a pelting agent, with calcination taking place in air at 700° C. to 800° C. for approximately 30 minutes.

15. A method according to claim 6 which includes the step of spraying a solution of the catalyst and carrier paste through an aligned shadow mask onto the track from both sides of the substrate.

16. A method according to any one of the preceding claims 6 to 15 in which the noble metal is platinum, the method including the step of annealing the catalytic gas detectors, when combined into a wafer, in a single step for stabilizing the electrical properties of the platinum, and for facilitating adhesion and cohesion of the catalyst and carrier and conditioning of the catalyst.

* * * * *